US005134063A

United States Patent [19]
Bochner

[11] Patent Number: 5,134,063
[45] Date of Patent: Jul. 28, 1992

[54] METHODS FOR DETECTION, IDENTIFICATION AND SPECIFICATION OF LISTERIAS

[75] Inventor: Barry Bochner, Alameda, Calif.

[73] Assignee: Biolog, Inc., Hayward, Calif.

[21] Appl. No.: 549,394

[22] Filed: Jul. 6, 1990

[51] Int. Cl.$^5$ .............................................. C12Q 1/02
[52] U.S. Cl. ........................................ 435/29; 436/63
[58] Field of Search ................... 435/29, 822; 424/7.1; 436/63

[56] References Cited

U.S. PATENT DOCUMENTS

| | | | |
|---|---|---|---|
| 3,930,956 | 1/1976 | Juni | 195/103.5 |
| 4,016,043 | 4/1977 | Schuurs et al. | 195/103.5 |
| 4,018,653 | 4/1977 | Mennen | 195/127 |
| 4,038,143 | 7/1977 | Juni | 195/100 |
| 4,129,483 | 12/1978 | Bochner | 195/100 |
| 4,235,964 | 11/1980 | Bochner | 435/34 |
| 4,424,279 | 1/1984 | Bohn et al. | 436/534 |
| 4,683,195 | 7/1987 | Mullis et al. | 435/6 |
| 4,683,202 | 7/1987 | Mullis | 435/91 |

FOREIGN PATENT DOCUMENTS

| | | |
|---|---|---|
| 0303309 | 7/1988 | European Pat. Off. |
| 0314294 | 9/1988 | European Pat. Off. |
| 0355147 | 1/1989 | European Pat. Off. |

OTHER PUBLICATIONS

Sprague et al. Biol. Abstracts, Abstract No. 55005 issued 1976.
Viswanath-Reddy, Biol. Abstracts, Abstract No. 50211 issued 1977.
Wilkinson, J. General Microbiology 1977:98:399-421.
Bergey's Manual, Williams & Wilkins, 1986, pp. 1235-1245.
Bochner Applied & Env. Microb. 1977, pp. 434-444 vol. 33 n 2.
H. Zinsser, *Microbiology (14th Edition)* Meredith Corp. pp. 751-753 (1968).
J. McLauchlin, J. Appl. Bacterio. 63:1 (1987).
A. R. Datta et al., Appl. Environ. Microbio. 54:2933 (1988).
J. Klinger et al., J. Assoc. Off. Anal. Chem. 71:669 (1988).
G. R. Siragusa and M. G. Johnson, Appl. Environ. Microbio. 56:1897 (1990).
J. A. Mattingly, J. Assoc. Off. Anal. Chem. 71:679 (1988).
Buchanan et al., Appl. Environ. Microbiol. 55:599 (1989).
Lachica, Appl Environ. Microbiol. 56:167 (1990).
A. Janik et al., J. Clin. Microbio. 4:71 (1976).
R. D. Lucas and R. E. Levin, Letters in Applied Microbiology 9:215 (1989).
Sambrook et al., *Molecular Cloning: A Laboratory Manual,* Cold Spring Harbor Laboratory, Cold Spring Harbor, pp. 310-361, Second Edition (1989).
Douillard and Hoffman, "Basic Facts About Lymphocyte Hybridomas", *Compendium of Immunology,* pp. 119-141, vol. II, Ed. by Schwartz (1981).
G. Kohler and C. Milstein, Nature 256:495 (1975).
G. Kohler and C. Milstein, European Journal of Immunology 6:511 (1976).
C. L. Reading, Journal of Immunological Methods 53:261 (1982).
F. Mat-Jan et al., J. Bacterio. 171:342 (1989).
E. Pradel et al., J. Bacterio. 172:802 (1990).
M. Futai and H. Kimura, J. Biol. Chem. 252:5820 (1977).
B. E. Britigan et al., J. Clin. Invest. 81:318 (1988).
D. J. Hassett and M. S. Cohen, FASEB Journal 3:2574 (1989).
H. Smith, J. General Microbio. 136:377 (1990).
J. Daniel et al., Mol. Gen. Genet. 190:452 (1983).
S. Kathariou et al., J. Bacterio. 169:1291 (1987).
B. J. Bachmann, Microbio. Rev. 54:130 (1990).
B. Skalka et al., J. Clin. Microbio. 25:503 (1982).
"Dehydrated Culture Media and Reagents for Microbiology", *DIFCO Manual, DIFCO Laboratories, p. 1047, Tenth Edition (1984).*
"Catalogue of Bacteria and Phages", *American Type Culture Collection,* American Type Culture Collection, p. 124, Seventeenth Edition (1989).
E. Juni, "Transformation Assays for Acinetobacter and Moraxella", *Nonfermentative Gram-Negative Rods: Laboratory Identification and Clinical Aspects,* pp. 341-356 (1985).

*Primary Examiner*—Douglas W. Robinson
*Assistant Examiner*—Jane Williams
*Attorney, Agent, or Firm*—Haverstock, Medlen & Carroll

[57] ABSTRACT

The present invention relates generally to differential carbon source metabolism in the genus *Listeria,* metabolic, biochemical, immunological and genetic procedures to measure said differential carbon source metabolism and the use of these produces to detect, isolate and/or distinguish species of the genus *Listeria* as well as detect, isolate and/or distinguish strains of species of *Listeria.* The present invention also contemplates test kits and enrichment media to facilitate these procedures.

12 Claims, No Drawings

METHODS FOR DETECTION, IDENTIFICATION AND SPECIFICATION OF LISTERIAS

FIELD OF THE INVETNION

The present invention relates to differential carbon source metabolism in Listeria as a basis for detection, identification and speciation.

BACKGROUND OF THE INVENTION

Bacteria belonging to the genus Listeria are Gram-positive, non-spore forming, motile rods characterized in part by their capability for growth over a wide range of temperatures (4° C. to 45° C.). H. Zinsser, Microbiology (14th Edition) (Meredith Corp. 968) pp. 751–753. The taxonomic relationships between the genus and allied Gram-positive taxa are not clear. Furthermore, since all Listeria show a high degree of DNA relatedness and very close similarity in biochemical, phenotypic and protein characteristics, there is disagreement in the field as to relationships between the identified species within the genus. B. J. Wilkinson and D. Jones, J. Gen. Microbio. 98:399 (1977). J. McLauchlin, J. Appl. Bacterio. 63:1 (1987).

Improved characterization of the genus would have important medical consequences. Outbreaks of listeriosis in the United States have been reported from Listeria-contaminated food. For example, in 981, there was a major outbreak associated with cabbage, in 1983 with milk and in 1985 with contaminated cheese. Listeria infection in humans can cause a variety of symptoms ranging from cold-like to flu-like but is especially dangerous to a fetus where it induces a 50% mortality rate.

With the focus on disease prevention, rapid screening of food samples for Listeria is of foremost concern to the food industry. Under current regulations, the presence of viable cells of any Listeria species in foods is a cause for concern. Thus, there is a need, as a first step, to improve the capability to detect, identify and speciate all species of the genus.

With the need to improve the capability to speciate all species, there is also the need to better understand the pathogenicity, if any, with each particular species. Nearly all of the reported cases of human infections by bacteria belonging to the genus Listeria have been caused by *Listeria monocytogenes*. See McLauchlin, J. Appl. Bacterio. 63:1 (1987). However, instances have been reported in which *Listeria ivanovii, Listeria innocua* and *Listeria seeligeri* have caused disease in humans. It is thus, as a second step, important to determine whether specific strains are associated with disease.

The Food and Drug Administration (FDA) in the United States and comparable agencies in other countries have promulgated standard laboratory methods to detect the presence of Listeria in environment or food specimens (eg milk). These methdos involve culturing an appropriately prepared sample on microbiological media under conditions favorable for growth of these organisms and unfavorable for other bacteria. Detection of bacteria of the Listeria genus is attempted by examining the resulting colonies for morphological and biochemical characteristics, a process that typically is started 48 hours after acquisition of the sample and takes between 9–19 days to complete.

Newer methods of detecting Listeria include a) nucleic acid probes capable of binding to the nucleic acid of particular species, and b) antibodies capable of reacting with antigens specific to particular species. See e.g. A. R. Datta et al., Appl. Environ. Microbio. 54:2933 (1988) (probes to a fragment of a presumptive hemolysin gene of *L. monocytogenes*); J. Klinger, J. Assoc. Off. Anal. Chem 71:669 (1988) (nucleic acid hybridization assay for Listeria in foods); European Patent Application No. 0355147 (corresponding to U.S. Ser. No. 227,402 and 143,490) (a probe directed to the hemolysin gene in *L. monocytogenes*); European Patent Application No. 314294 (corresponding to U.S. Ser. No. 965,510) (probes to rRNA of L. monocyvtogenes); G. R. Siragusa and M. G. Johnson, Appl. Environ. Microbio. 56:1897 (1990) (monoclonal antibodies to an antigen shared with three Listeria species); J. A. Mattingly, J. Assoc. Off. Anal. Chem. 71:679 (1988) (antibody-based assay for detection of *L. monocytogenes*); European Patent Application No. 0303309 (corresponding to U.S. Ser. No. 36,619) (antibodies to heat-treated extracts of Listeria).

The present invention now provides a method capable of (1) detecting bacteria of the genus Listeria and (2) distinguishing between species of the genus Listeria. The method of the present invention has the advantage over previous methods in that it is easier, simpler and less expensive. It is also faster than the current biochemical characterization procedures which involve slow fermentation reactions detected with pH indicators.

SUMMARY OF THE INVENTION

In one embodiment, the present invention provides a method for detecting a species of the genus Listeria comprising exposing a sample suspected of containing microorganisms belonging to the genus Listeria to a metabolically effective amount of one or more carbon sources capable of being metabolized by a subset of species of Listeria, for a time and under conditions sufficient for the subset to metabolize the carbon source, and detecting any metabolism of the carbon source by assaying for respiration by the microorganisms, thereby determining the presence of the subset of species.

In another embodiment, the method further comprises, prior to the exposing step, subjecting the sample to an enrichment treatment which will enhance the population of the genus Listeria in the sample.

In another embodiment, the carbon sources are selected from the group consisting of mannitol, D-gluconic acid, L-malic acid, 5'AMP, β-methyl glucoside, glycerol, D-xylose, L-rhamnose, xylitol, sucrose, α-D-lactose, L-lactic acid, and hexose-phosphate.

In another embodiment, the carbon sources comprise a panel of carbon sources comprised of L-lactic acid and xylitol.

In another embodiment, the carbon sources comprise a panel of carbon sources comprised of hexose-phosphate and xylitol.

The present invention also contemplates a test kit for the detection of a species of the genus Listeria or a strain of a species of the genus Listeria comprising at least one compartment containing at least one carbon source capable of being metabolized by a subset of species of the genus Listeria, wherein the carbon source is selected from the group consisting of mannitol, D-gluconic acid, L-malic acid, 5'AMP, β-methyl glucoside, glycerol, D-xylose, L-rhamnose, xylitol, sucrose, α-D-lactose, L-lactic acid, and hexose-phosphate.

The present invention also contemplates a test kit for the detection of a species of the genus Listeria or a strain of a species of the genus Listeria comprising a plurality of compartments containing a plurality of carbon sources capable of being metabolized by a subset of species of the genus Listeria, wherein the carbon sources comprise a panel of carbon sources, each carbon source of said panel in separate compartments, comprising L-lactic acid and xylitol.

The present invention also contemplates a test kit for the detection of a species of the genus Listeria or a strain of a species of the genus Listeria comprising a plurality of compartments containing a plurality of carbon sources capable of being metabolized by a subset of species of the genus Listeria, wherein the carbon sources comprise a panel of carbon sources, each carbon source of said panel in separate compartments, comprising hexose-phosphate and xylitol.

The present invention further provides a method for detecting a species of the genus Listeria comprising exposing a sample suspected of containing microorganisms belonging to the genus Listeria to a metabolically effective amount of one or more carbon sources capable of being metabolized by L. monocytogenes and L. ivanovii but not for metabolism by other species of Listeria, for a time and under conditions sufficient for metabolism by L. monocytogenes and L. ivanovii, and detecting any metabolism of said carbon source, thereby determining the presence of L. monocytogenes and/or L. ivanovii.

In one embodiment of this method, the method further comprises, prior to the exposing step, subjecting the sample to an enrichment treatment which will enhance the population of the genus Listeria in the sample.

In one embodiment of this method, the carbon sources are selected from the group consisting of L-lactic acid and hexose-phosphate.

The present invention also contemplates a method for detecting a species of the genus Listeria comprising exposing a sample suspected of containing microorganisms belonging to the genus Listeria to a metabolically effective amount of one or more carbon sources capable of being metabolized by a subset of species of the genus Listeria, but not metabolized by L. monocytogenes or L. ivanovii, for a time and under conditions sufficient for metabolism by the subset of species, and detecting any metabolism of the carbon source, thereby determining the presence of a species other than L. monocytogenes and L. ivanovii.

In one embodiment of this method, the method further comprises, prior to the exposing step, subjecting the sample to an enrichment treatment which will enhance the population of the genus Listeria in the sample.

In one embodiment of this method, the carbon sources are selected from the group consisting of mannitol, D-gluconic acid, and L-malic acid.

In another embodiment of this method, the carbon sources comprise a panel of carbon sources comprised of mannitol, D-gluconic acid, and L-malic acid.

The present invention also contemplates an enrichment medium for species of the genus Listeria comprising, in liquid or semi-solid form, a basal medium having all the constituents selective for growth of the genus Listeria, and a growth effective amount of one or more carbon sources capable of being utilized by a subset of species of the genus Listeria, wherein the carbon source is selected from the group congsisting of mannitol, D-gluconic acid, L-malic acid, 5'AMP, $\beta$-methyl glucoside, glycerol, D-xylose, L-rhamnose, xylitol, sucrose, $\alpha$-D-lactose, L-lactic acid, and hexose-phosphate.

In the sense that, heretofore, no known method of detecting the genus Listeria allowed for complete speciation, one aspect of the present invention is an improvement. In a method for detecting microorganisms of the genus Listeria wherein a sample suspected of containing microorganisms belonging to the genus Listeria is subjected to an enrichment treatment capable of enhancing the population of the genus Listeria in the sample, the improvement comprises, thereafter exposing the sample to a metabolically effective amount of one or more carbon sources capable of being metabolized by a subset of species of Listeria, for a time and under conditions sufficient for the subset to metabolize the carbon source, and detecting any metabolism of the carbon source by assaying for respiration by the microorganisms, thereby determining the presence of the subset of species.

DETAILED DESCRIPTION OF THE INVENTION

The present invention is predicated in part on the surprising discovery that microorganisms of a species of the genus Listeria can be distinguished from microorganisms of another species of the genus Listeria as well as from non-Listeria microorganisms by differential metabolism of a variety of novel carbon sources. The present invention is also based on the surprising discovery that specific strains of species of the genus Listeria can be distinguished from other strains of the same species by differential metabolism of a variety of carbon sources.

The present invention contemplates that the differential metabolism can be observed at the biochemical level by measuring parameters such as respiration (e.g. measured colorimetrically) and microbial growth (e.g. measured turbidimetrically) The present invention also contemplates that this differential metabolism can also be observed a) using an indicator strain of Listeria that is competent for transformation, b) using nucleic acid probes, or c) employing specific antibodies.

Unless otherwise specified, the generic term "Listeria" is used herein to refer to all species of the genus including, but not limited to, L. monocytoqenes, L. ivanovii, L. innocua, L. welshimeri, L. seeligeri, L. gravi, and L. murrayi.

With respect to the phrase "microorganisms suspected of being of the genus Listeria" it is not meant that the microorganisms must be homogeneous. It may comprise a heterogenous mixture of Listeria species or strains of one or more species of Listeria and may contain microorganisms not belonging to the genus Listeria. On the other hand, it may comprise homogenous and/or substantially pure cultures of one or more species or strains of Listeria.

The term "sample" in the present specification and claims is used in its broadest sense. On the one hand it is meant to include a specimen or culture. On the other hand, it is meant to include both biological and environmental samples.

Biological samples may be animal, including human, fluid or tissue, food products and its ingredients such as dairy, vegetable and meat produce, and waste. Environmental samples include environmental material such as surface matter, soil, water and industrial samples.

Whether a biological or environmental sample, a sample suspected of containing Listeria may or may not first be subjected to an enrichment means to create a culture of microorganisms suspected of being of the genus Listeria. By enrichment means or enrichment treatment the present invention contemplates (i) conventional techniques for isolating Listeria away from other microorganisms and (ii) novel techniques for isolating Listeria away from other microorganisms involving the use of one or more of the carbon sources of the present invention. Importantly, it is not intended that the present invention be limited only to one enrichment step or type of enrichment means. For example, it is within the scope of the present invention to, following subjecting a sample to a conventional enrichment means, subjecting the resulting preparation to further purification such that pure or substantially pure cultures of the Listeria species or strain of species are produced.

With respect to a "culture" it is not meant that the enrichment means must only be in a liquid phase. The present invention contemplates a variety of types of enrichment means (whether in or on a liquid or semisolid medium).

The carbon compounds of choice in accordance with the present invention are those which some species of the genus Listeria can utilize as a carbon source for growth and/or respiration but which are unable or substantially unable to be metabolized by other species of the same genus.

In one embodiment, the present invention involves using L-lactic acid and/or a hexose phosphate (e.g. glucose-phosphate, mannose-phosphate and fructose-phosphate) as the carbon sources of choice. Where a hexose phosphate is used, glucose-1-phosphate is a preferred sugar phosphate (primarily because of its stability, purity and commercial availability). Such carbon sources have heretofore never been reported useful for Listeria detection or speciation.

In another embodiment, the present invention also describes the use of xylitol as a carbon source. Xylitol (to be distinguished from D-xylose) is a carbon source heretofore never reported useful for Listeria detection or speciation.

In another embodiment, the present invention also describes the use of adenosine 5'-monophosphate (5'AMP) as a carbon source. 5'AMP is a carbon source heretofore never reported useful for Listeria detection or speciation.

In another embodiment, the present invention also describes the use of glycerol, β-methyl glucoside, D-gluconic acid and/or L-malic acid as carbon sources. Heretofore, it was reported that all of the species could utilize glycerol and β-methyl glucoside, that none of the Listeria species could utilize gluconic acid, and that malic acid was primarily utilized by L. monocytogenes. J. General Microbio. 98:399 (1977). Our findings are not in agreement with many aspects of this report. In the case of malic acid, the report indicates that a mixture of the D- and L-isomers was used. The usefulness of β-methyl glucoside for speciating Listerias has not heretofore been reported.

Finally, the present invention describes the use of the above-named carbon sources together with one or more carbon sources heretofore tested in the detection and/or identification of Listeria (e.g., mannitol, D-xylose, sucrose, α-D-lactose and L-rhamnose). This is done, however, with the understanding that it is not intended that the present invention be limited to the use of known useful Listeria carbon sources in conjunction with the novel sources described earlier. Furthermore, the present invention extends to chemical, biochemical, biological and/or functional equivalents or homologues of the aforementioned carbon sources including any structural modifications thereto provided that said equivalents, homologues or modified carbon sources are utilized by some species of the genus Listeria. The carbon sources of the present invention may also be added as its corresponding salt. Accordingly, reference to L-lactic acid, for example, includes its corresponding salt forms.

The carbon sources may be used singularly or in combination with other carbon sources. However, in some circumstances, two or more carbon sources may not be appropriate in combination due to catabolite repression or utilization by other non-Listeria organisms.

Antibiotics or other selective agents (e.g. lithium salts) may be used in conjunction with the present invention to inhibit non-Listeria organisms and/or to promote growth of Listeria bacteria.

A preferred embodiment of the present invention contemplates a method for detecting a species of the genus Listeria in a biological sample comprising, subjecting said sample to an enrichment means so as to create a culture of microorganisms suspected of being of the genus Listeria, exposing said culture separately or together to amounts of carbon sources effective for metabolism, wherein the carbon sources are selected from the group consisting of L-lactic acid, glucose-1-phosphate, xylitol, D-gluconic acid, L-malic acid, 5'AMP, glycerol, and β-methyl glucoside, and wherein the exposure is for a time and under conditions sufficient for metabolism, and then detecting metabolism.

Another preferred embodiment of the present invention contemplates a method for detecting a species of the genus Listeria in a biological sample comprising, subjecting said sample to an enrichment means so as to create a culture of microorganisms suspected of being of the genus Listeria, exposing said culture to a panel of carbon sources consisting of mannitol, L-lactic acid, glucose-1-phosphate, xylitol, 5'AMP, β-methyl glucoside, L-rhamnose and D-xylose, wherein the carbon sources are in amounts effective for metabolism and wherein said exposure is for a time and under conditions sufficient for metabolism, and detecting metabolism.

In the practice of the present invention it has been found that L-lactic acid and glucose-1-phosphate as carbon sources are useful to differentiate *L. monocytogenes* and *L. ivanovii* from *L. innocua, L. welshimeri, L. seeligeri, L. gravi,* and *L. murravi*; xylitol as a carbon source is useful to differentiate *L. monocytogenes, L. innocua, L. welshimeri* and *L. seeligeri,* from *L. ivanovii, L. oravi,* and *L. murravi*; 5'AMP, D-xylose, mannitol, D-gluconic acid and L-malic acid as carbon sources are useful to differentiate *L. oravi* and *L. murravi* from *L. monocytogenes, L. ivanovii, L. innocua, L. welshimeri* and *L. seeligeri*; L-rhamnose as a carbon source is useful to distinguish *L. monocytogenes, L. innocua* and *L. welshimeri.* from other species of Listeria. Lastly, glycerol and β-methyl glucoside as carbon sources are useful to distinguish *L. ivanovii* and *L. gravi* from other species of Listeria since they give a negative or a very weak positive reaction with these. (See Table 1).

In accordance with one embodiment of the present invention, the carbon sources are added to a reaction vessel containing basal medium and other constituents as required for growth. "Basal medium" as used herein refers to a medium suitable for growth of Listeria but which does not contain sufficient amounts of a carbon source for metabolism. More conveniently, the carbon sources are added separately or in combination into a series of reaction vessels such that a range of carbon sources and/or various combinations of carbon sources can be tested at one time. Alternatively, the reaction vessel(s) may contain the required carbon source to which basal medium is then added or the carbon source may be added to the basal medium already in the reaction vessel. The order of addition of the components in accordance with the present invention is not critical. In addition to the carbon source and basal medium and other components necessary for growth, each reaction vessel may also contain one or more indicator molecules such as, but not limited to, a redox indicator (e.g. tetrazolium), a pH indicator, and various dyes and the like. These approaches are fully described in U.S. Pat. Nos. 4,129,483 and 4,235,964 to Barry R. Bochner, hereby incorporated by reference. A generalized indicator useful for practice of the present invention is also described by Bochner and Savageau. See B. Bochner and M. Savageau, Applied and Environmental Microbiology, 33:434 (1977).

Analysis of differential carbon source metabolism as contemplated herein is conveniently conducted using a test kit. In a preferred embodiment of the present invention, the test kit comprises a microtiter plate containing an appropriate basal medium. The required carbon source is then added to each compartment at the appropriate concentration. Each compartment may, along with the basal medium, also contain an appropriate indicator or the compartment may be so constructed that growth is measurable turbidmetrically. Alternatively, the indicator may be added separately. In any event, the preferred use of the basal medium, carbon source, indicator and any other chemical (or mixture of chemicals) is in a dry form in the microplate.

It is preferred in this case, that the microorganisms suspected to be Listeria are prepared as required in saline or other suitable diluent and then each compartment of the plate inoculated.

Plates useful in the practice of the present invention as a kit are commercially available from Biolog, Inc., Hayward, Calif. For example, the Biolog MT Micro-Plate ™ is particularly useful. The MT plate is a 96-well microplate designed to test the ability of an inoculated microorganism suspension to utilize (oxidize) a panel of different carbon sources. Each well of the panel contains a tetrazolium redox dye and a buffered nutrient medium that has been developed and optimized for a wide variety of bacteria. If used in the practice of the present invention, the carbon sources of the present invention may be added to the MT plates either before or after inoculating with a microorganism suspension. For example, with a Biolog MT MicroPlate, about 0.6 mg of carbon source (e.g. 15 ul of a 4% stock solution) may be added to each well giving a resulting concentration of 0.4% (w/v). After addition the carbon source may be dried. The Biolog's MT MicroPlate ™ may be arranged so that there is one or more negative control wells with no carbon source and/or one or more positive control wells containing a carbon source (e.g., salicin) or a mixture of carbon sources such that all Listeria strains will give a positive reaction. The remaining wells of a set contain individual carbon sources or a combination of carbon sources that may or may not be metabolized. After inoculation, the reaction vessel, compartment or indicator plate is then incubated at an appropriate temperature or range of temperatures, preferably between 25° and 40° C. and most preferably between 30° and 37° C. for 1 to 24 hours. Many of the carbon source reactions are apparent even by 1 hour.

As noted earlier, a sample suspected of containing Listeria may be first subjected to an enrichment means and this enrichment means may involve i) conventional techniques for isolating Listeria away from other microorganisms or ii) novel techniques for isolating Listeria away from other microorganisms involving the use of one or more of the carbon sources of the present invention.

Where conventional techniques are used in the enrichment step, a sample suspected to contain one or more species of Listeria may be inoculated onto a semi-solid medium (e.g. an agar plate) as an enrichment means. The inoculated semi-solid medium is then optionally exposed to conditions which allow for growth of the Listeria. Conventional enrichment means may be selected from any available to those skilled in the art, including but not limited to, the following: original McBride Listeria agar formulations, modified McBride Listeria agar formulation, LiCl-phenylethanol-moxalactam (LPM) agar, acriflavine-ceftazidime agar, Rodriguez isolation agar (RISA), modified Vogel-Johnson (MVJ) agar and cyclohexanedione-nalidixic acid-phenylethanol agar and their liquid forms. Most preferably, the enrichment means is LPM or MVJ. A general discussion of other suitable media for Listeria can be found in Loessner et al., *Appl. Environ, Microbiol.* 54: 3003-3007, 1988; Buchanan et al., *Appl. Environ. Microbiol.* 55: 599-603, 1989; Lachica, *Appl Environ. Microbiol.* 56: 167-169, 1990.

Where novel techniques of the present invention are used in the enrichment step, a sample suspected to contain one or more species of Listeria may be inoculated onto a semi-solid medium (e.g. an agar plate). The inoculated semi-solid medium is then optionally exposed to conditions which allow for growth of the Listeria. In any event, microorganisms present on the plate may then be replica-plated or transferred by other means to liquid or semi-solid growth media containing a carbon source of the present invention which may be utilized by one or more species of Listeria but not by other species of the same genus.

Alternatively, using novel enrichment techniques of the present invention, the sample may be inoculated directly into or onto a liquid or semi-solid growth medium containing, as sole carbon source, a carbon source of the present invention capable of being utilized by one or more species of Listeria but not by other species of the same genus.

In one embodiment, utilization of a carbon source is measured by the formation of one or more colonies of the pathogenic strain. The amount of carbon source added to the reaction vessel will be that required for growth of the Listeria bacterium By "growth" it is meant that the bacterium has undergone at least one doubling, the only requirement being that sufficient doubling must take place in order for the particular indicator to detect growth, or for there to be sufficient growth to be measured turbidimetrically. When a semi-solid growth medium is used, sufficient growth is required to observe one or more colonies. Typically, the final concentration of carbon source is from about 0.05 to about 5.0% (w/v) and preferably from about 0.20 to about 10% (w/v). Most preferably, the concentration of carbon source is approximately 0.4% (w/v). However, the concentration may be varied depending on the organism to be detected, availability of carbon source, ease of solubility and indicator selected.

According to this embodiment of the present invention, there is provided an enrichment or selection growth medium for one or more species of Listeria comprising in liquid or semi-solid form, a basal medium having all the constituents required for growth of Listeria except for a carbon source and a growth effective amount of one or more carbon sources capable of being utilized by one or more species of Listeria but not by other species of the same genus.

The present invention also contemplates a novel enrichment means wherein the aforementioned conventional media are used, but wherein the principle carbon source is replaced by one or more of the carbon sources of the present invention.

OTHER DETECTION METHODS

As noted earlier, the present invention contemplates that the differential metabolism can be observed at the metabolic or biochemical level by measuring parameters such as respiration (e.g. measured colorimetrically) and microbial growth (e.g. measured turbidimetrically). On the other hand, the present invention contemplates that this capability for differential metabolism can also be observed by other detection methods including (a) using an indicator strain of Listeria in a genetic repair assay, (b) using nucleic acid probes in a hybridization assay, or (c) employing specific antibodies in an immunological assay or stain.

(a) Genetic Repair Assay

Another assay contemplated by the present invention allows the rapid screening of biological samples for the presence or absence of pathogenic strains of Listeria. The assay provides a simple yes/no test whether or not a biological sample, such as food, contains a pathogenic strain of Listeria.

In one embodiment, an indicator strain of Listeria is rendered competent for transformation by naked DNA and also carries a mutation affecting expression of one or more enzymes or other proteins involved in the uptake or metabolism of a carbon source by pathogenic strains of Listeria and which carbon sources are not metabolized by non-pathogenic strains of Listeria (examples of such carbon sources may be L-lactic acid or hexose-phosphate; see Table 1 and accompanying discussion, below). The indicator strain may also express a selective marker such as but not limited to resistance to an antibiotic or other antimicrobial compound including a heavy metal. The biological sample is then subjected to genetic extraction meaning that the DNA of any microorganism therein is released by such means as enzymes, organic extraction, detergents or sonic disruption. Further purification and partial digestion of the genetic extract may then be required depending on the biological sample, time and degree of sensitivity desired.

The genetic extract is then mixed with an excess of the competent indicator strain for a time and under conditions sufficient to allow transformation of the indicator strain with any Listeria DNA. The mixture is then added dropwise or by other means to the semi-solid or liquid medium. The mixture is introduced to the medium containing, as sole carbon source, the carbon source on which the mutation it carries prevents it from growing. The medium is then incubated and examined for growth. If growth does occur, the indicator strain must have been transformed with DNA from a pathogenic strain and the mutation preventing the indicator strain from growing on the sole carbon source in the medium repaired. Appropriate controls are also run to verify that the genetic lesion did not revert and that the sample extract containing DNA was not contaminated with viable microorganisms.

Many variations to the above assay may be made without departing from the scope of the present invention. For example, rather than the DNA entering the indicator strain by transformation, it might enter by transduction following an in vitro phage packaging reaction, or by conjugation, possibly with a non-Listeria competent strain that would take up naked DNA and transfer it by conjugation into the Listeria indicator strain. In the latter case, the growth medium may additionally contain an agent to prevent growth of the non-Listeria bacterium. Transformation techniques are disclosed, for example, in U.S. Pat. Nos. 3,930,956 and 4,038,143 to E. Juni, hereby incorporated by reference. Other approaches are disclosed in A. Janick et al., J. Clin. Microbio. 4:71 (1978). Transformation techniques for Listeria are disclosed in Lucas and Levin, Letters in Applied Microbiology 9:215 (1989).

Accordingly, this aspect of the present invention contemplates a means for detecting a potentially pathogenic strain of a species of the genus Listeria in a biological or environmental sample comprising (1) providing a competent strain of Listeria carrying a mutation in or near a gene encoding an enzyme or other protein or parts thereof involved in or associated with the uptake or metabolism of a carbon source used by a potentially pathogenic strain of Listeria, or in or near a promoter region, regulatory gene or other control sequence or parts thereof for expression of said enzyme or other protein, said mutation resulting in said enzyme or other protein not being produced or being produced in inactive form, thereby said competent strain of Listeria being unable to grow on said carbon source, (2) contacting said competent strain of Listeria carrying said mutation with a genetic extract of said biological or environmental sample for a time and under conditions sufficient for said competent strain of Listeria to be transformed with DNA of a potentially pathogenic strain of Listeria, if present, in said genetic extract of the sample, wherein said DNA is capable of repairing the mutation in said competent strain of Listeria and (3) detecting growth of said transformed Listeria on the carbon source for which previously the strain could not grow.

Another aspect of the present invention provides a means for detecting a potentially pathogenic strain of a species of the genus Listeria in a biological or environmental sample comprising (1) providing an indicator strain of Listeria carrying a mutation in or near a gene encoding an enzyme or other protein or parts thereof involved in or associated with the metabolism of a carbon source used by a potentially pathogenic strain of Listeria, or in or near a promoter region, regulatory gene or other control sequence or parts thereof for expression of said enzyme or other protein, said mutation resulting in said enzyme or other protein not being produced or being produced in inactive form, thereby said indicator strain of Listeria being unable to grow on said carbon source, (2) contacting said indicator strain of Listeria carrying said mutation with a conjugative donor strain or a phage for a time and under conditions sufficient for said indicator strain of Listeria to be conjugated or transduced with DNA from a potentially pathogenic strain of Listeria, if present, in said sample, wherein DNA transferred is capable of repairing the mutation in said indicator strain of Listeria, and (3)

detecting growth of said repaired Listeria on the carbon source for which previously the strain could not grow.

(b) Hybridization Assay

Another embodiment of the present invention relates to a nucleic acid molecule capable of hybridizing to genetic material contained in a genetic extract of one or more species of the genus Listeria but which does not hybridize to genetic material in other species of the same genus. Ideally, the nucleic acid molecule will hybridize under predetermined stringency levels to genetic material, at least part of which, encodes an enzyme or protein or portions thereof or defines a promoter region, regulatory gene or other control sequence or parts thereof for expressing enzymes or other proteins associated with the metabolism by particular species of Listeria of the aforementioned carbon source compounds, said genetic material substantially absent in other species of the same genus.

In this regard, the genetic material may be DNA or RNA. When the genetic material is mRNA, the bacterial cells may first need to be inoculated in the presence of the subject carbon source for a time and under conditions sufficient to permit transcription of the DNA into mRNA. A genetic extract comprises the genetic material (i.e. DNA or RNA) or various parts thereof from a particular cell.

"Hybridization" is used herein in its broadest sense and refers to the formation of duplexes between completely or partially complementary nucleotide sequences by Watson-Crick base-pairing. The stringency conditions used may very depending on the base composition of the probe-target duplex as well as by the level and geometry of mispairing between the two nucleic acids.

The genetic detection of a species of Listeria may be accomplished in a number of ways. In one preferred embodiment, the species or strain to be identified is grown on semi-solid media into one or more colonies. The colonies are transferred onto nitrocellulose paper or other suitable material and subjected to dot blot analysis or similar hybridization procedure. Techniques useful for this type of genetic screening can be found in *Molecular Cloning: A Laboratory Manual*, Sambrook et al eds, Cold Spring Harbor Laboratory, Cold Spring Harbor, second edition, 1989.

The nucleic acid probes may be prepared by any number of means. For example, an enzyme or protein involved in or associated with the metabolism of a carbon source by one or more species of Listeria and which is absent from other species of the same genus is first purified and a contiguous series of amino acids in said enzyme or other protein determined. For example, the N-terminal amino acid sequence is ascertained and a probe comprising nucleotide sequence is the prepared based on the amino sequence. Generally a range of probes is produced. Using Southern or Northern blots, a probe capable of hydridizing to genetic material in one or more species of Listeria but not genetic material from other species is selected.

Conveniently, a biological sample may be screened for the presence of a species of Listeria by immobilizing bacteria contained in said biological sample onto a semi-solid support and then subjecting said immobilized bacteria to detection means by using a labelled nucleotide probe. The label may be a radioactive isotope, or biotinylated molecule or other detectable marker.

This aspect of the present invention is conveniently provided in kit form comprising a compartment or a multiplicity of compartments adapted to receive a biological sample suspected to contain a species of Listeria, a second compartment or multiplicity of compartments adapted to contain one or more nucleic acid molecules capable of hybridizing at pre-determined stringency conditions to genetic material encoding one or more enzymes or other protein or portions thereof or defining a promoter region, regulatory gene or other control sequence or parts thereof for expressing enzymes or other proteins involved in or associated with the metabolism of one or more carbon sources by one or more species of Listeria and which genetic material is absent or substantially absent from another species of the same genus, said nucleic acid molecules labelled with a reporter molecule.

In further accordance with this aspect of the present invention, the sensitivity and/or ease of performing this assay may be enhanced by using the polymerase chain reaction (PCR) as described by K.B. Mullis et al. in U.S. Pat. Nos. 4,683,195 and 4,683,202, hereby incorporated by reference. To this end, the present invention extends to nucleotide probes or primers useful in the PCR to detect the aforementioned DNA or RNA. Accordingly, the kit contemplated herein may contain additional compartments adapted to contain the components for PCR including the nucleotide primers.

(c) Immunological Assay

A further aspect of the present invention relates to the immunological detection of a species of Listeria using antibodies directed to an enzyme or other protein present in said species but absent in other species of the same genus and which are involved in or associated with the utilization of one or more carbon sources, said enzyme or protein absent in said other species of the same genus. The enzyme or protein is purified from the species by conventional techniques and used to prepare specific antibodies. Such antibodies are useful in developing detection assays (immunoassays) for the enzyme or protein. The presence of the enzyme or protein in a biological sample or an extract thereof is indicative of the presence of a species of Listeria.

In the following methods, where specific enzymes or proteins are not secreted from the bacterium to be detected, the cells are disrupted by treatments which include sonic disruption, osmotic change or use of agents such organic solvents, detergents, enzymes and the like.

Furthermore, immunological equivalents of the enzymes or proteins may be used to facilitate the production of antibodies. Additionally, a mixture of enzymes or proteins may be used to facilitate the production of antibodies. A mixture of enzymes or proteins may also be used to develop antibodies.

The antibodies may be monoclonal or polyclonal. It is within the scope of this invention to include any second antibodies (monoclonal or polyclonal) directed to the first antibodies discussed above. Both the first and second antibodies may be used in the detection assays or a first antibody may be used with a commercially available anti-immunoglobulin antibody. An antibody as contemplated herein includes any antibody specific to any region of an enzyme or other protein exclusively involved in the metabolism of a carbon source by one or more species of Listeria and which is absent from another species of the same genus.

Both polyclonal and monoclonal antibodies are obtainable by immunization with the enzyme or protein and either type is utilizable for immunoassays. The methods of obtaining both types of sera are well known in the art. Polyclonal sera are less preferred but are relatively easily prepared by injection of a suitable laboratory animal with an effective amount of the purified enzyme or protein, or antigenic parts thereof, collecting serum from the animal, and isolating specific sera by any of the known immunoadsorbent techniques. Although antibodies produced by this method are utilizable in virtually any type of immunoassay, they are generally less favored because of the potential heterogeneity of the product.

The use of monoclonal antibodies in an immunoassay is particularly preferred because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art. (See, for example Douillard and Hoffman, Basic Facts about Hybridomas, in *Compendium of Immunology* Vol II, ed. by Schwartz, 1981; Kohler and Milstein, *Nature* 256: 495-499, 1975; *European Journal of Immunology* 6: 511-519, 1976).

Unlike preparation of polyclonal sera, the choice of animal is dependent on the availability of appropriate immortal lines capable of fusing with lymphocytes. Mouse and rat have been the animals of choice in hybridoma technology and are preferably used. Humans can also be utilized as sources for sensitized lymphocytes if appropriate immortalized human (or nonhuman) cell lines are available. For the purpose of the present invention, the animal of choice may be injected with an antigenic amount, for example, from about 0.1 mg to about 20 mg of the enzyme or protein or antigenic parts thereof. Usually the injecting material is emulsified in Freund's complete adjuvant. Boosting injections may also be required. The detection of antibody production can be carried out by testing the antisera with appropriately labelled antigen. Lymphocytes can be obtained by removing the spleen of lymph nodes of sensitized animals in a sterile fashion and carrying out fusion. Alternatively, lymphocytes can be stimulated or immunized in vitro. as described, for example, in Reading, *Journal of Immunological Methods* 53: 261-291, 1982.

A number of cell lines suitable for fusion have been developed and the choice of any particular line for hybridization protocols is directed by any one of a number of criteria such as speed, uniformity of growth characteristics, deficiency of its metabolism for a component of the growth medium, and potential for good fusion frequency.

Intraspecies hybrids, particularly between like strains, work better than interspecies fusions. Several cell lines are available, including mutants selected for the loss of ability to secrete myeloma immunoglobulin.

Cell fusion can be induced either by virus, such as Epstein-Barr or Sendai virus, or polyethylene glycol. Polyethylene glycol (PEG) is the most efficacious agent for the fusion of mammalian somatic cells. PEG itself may be toxic for cells and various concentrations should be tested for effects on viability before attempting fusion. The molecular weight range of PEG may be varied from 1000 to 6000. It gives best results when diluted to from about 20% to about 70% (w/w) in saline or serum-free medium. Exposure to PEG at 37° C. for about 30 seconds is preferred in the present case, utilizing murine cells. Extremes of temperature (i.e., about 45° C.) are avoided, and preincubation of each component of the fusion system at 37° C. prior to fusion can be useful. The ratio between lymphocytes and malignant cells is optimized to avoid cell fusion among spleen cells and a range of from about 1:1 to about 1:10 is commonly used.

The successfully fused cells can be separated from the myeloma line by any technique known by the art. The most common and preferred method is to choose a malignant line which is Hypoxthanine Guanine Phosphoribosyl Transferase (HGPRT) deficient, which will not grow in an aminopterin-containing medium used to allow only growth of hybrids and which is generally composed of hypoxthanine $1\times10^{-4}$M, aminopterin $1\times10^{-5}$M, and thymidine $3\times10^{-5}$M, commonly known as the HAT medium. The fusion mixture can be grown in the HAT-containing culture medium immediately after the fusion 24 hours later. The feeding schedules usually entail maintenance in HAT medium for two weeks and then feeding with either regular culture medium or hypoxthanine, thymidine-containing medium.

The growing colonies are then tested for the presence of antibodies that recognize the antigenic preparation. Detection of hybridoma antibodies can be performed using an assay where the antigen is bound to a solid support and allowed to react to hybridoma supernatants containing putative antibodies. The presence of antibodies may be detected by "sandwich" techniques using a variety of indicators. Most of the common methods are sufficiently sensitive for use in the range of antibody concentrations secreted during hybrid growth.

Cloning of hybrids can be carried out after 21-23 days of cell growth in selected medium. cloning can be preformed by cell limiting dilution in fluid phase or by directly selecting single cells growing in semi-solid agarose. For limiting dilution, cell suspensions are diluted serially to yield a statistical probability of having only one cell per well. For the agarose technique, hybrids are seeded in a semi-solid upper layer, over a lower layer containing feeder cells. The colonies from the upper layer may be picked up and eventually transferred to wells.

Antibody-secreting hybrids can be grown in various tissue culture flasks, yielding supernatants with variable concentrations of antibodies. In order to obtain higher concentrations, hybrids may be transferred into animals to obtain inflammatory ascites. Antibody-containing ascites can be harvested 8-12 days after intraperitoneal injection. The ascites contain a higher concentration of antibodies but include both monoclonals and immunoglobulins from the inflammatory ascites Antibody purification may then be achieved by, for example, affinity chromatography.

The presence of the enzyme or protein contemplated herein in a species of Listeria may be accomplished in a number of ways such as on a semi-solid growth medium plate where colonies of bacteria are tested, by for example, the Western blotting procedure. Alternatively, other semi-solid supports may be employed onto which the biological sample has been immobilized. In another method, the biological sample is contacted with a solid support already containing a specific antibody. In any event the principle behind the assay is the same. A wide range of immunoassay techniques are available as can be seen by reference to U.S. Pat. Nos. 4,016,043, 4,424,279 and 4,018,653. This, of course, includes both single-site and two-site, or "sandwich", assays of the non-competitive types, as well as in the traditional competitive binding assays.

Sandwich assays are among the most useful and commonly used assays and are favored for use in the present invention. A number of variations of the sandwich assay technique exist, and all are intended to be encompassed by the present invention. Briefly, in a typical forward assay, an unlabelled antibody is immobilized on a solid substrate and the sample to be tested brought into contact with the bound molecule. After a suitable period of incubation, for a period of time sufficient to allow formation of an antibody-antigen secondary complex, a second antibody specific to the antigen, labelled with a reporter molecule capable of producing a detectable signal is then added and incubated, allowing time sufficient for the formation of a tertiary complex of antibody-antigen-labelled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of hapten. Variations on the forward assay include a simultaneous assay, in which both sample and labelled antibody are added simultaneously to the bound antibody. These techniques are well known to those skilled in the art, including any minor variations as will be readily apparent.

In the typical forward sandwich assay, a first antibody having specificity for the enzyme or protein, or antigenic parts thereof, contemplated in this invention, is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated at 25° C. for a period of time sufficient to allow binding of any subunit present in the antibody. The incubation period will vary but will generally be in the range of about 2–40 minutes. Following the incubation period, the antibody subunit solid phase is washed and dried and incubated with a second antibody specific for a portion of the hapten. The second antibody is linked to a reporter molecule which is used to indicate the binding of the second antibody to the hapten.

An alternative method involves immobilizing the target molecules in the biological sample and then exposing the immobilized target to specific antibody which may or may not be labelled with a reporter molecule. Depending on the amount of target and the strength of the reporter molecule signal, a bound target may be detectable by direct labelling with the antibody. Alternatively, a second labelled antibody, specific to the first antibody is exposed to the target-first antibody complex to form a target-first antibody-second antibody tertiary complex. The complex is detected by the signal emitted by the reporter molecule.

By "reporter molecule" as used in the present specification, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores, luminescent molecules or radionuclide containing molecules (i.e. radioisotopes).

In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, beta-galactosidase and alkaline phosphatase, amongst others. The substrates to be used with the specific enzymes are generally chosen for the production, upon hydrolysis by the corresponding enzyme, of a detectable color change. For example, p-nitrophenyl phosphate is suitable for use with alkaline phosphatase conjugates; for peroxidase conjugates, 1,2-phenylenediamine, 5-aminosalicyclic acid, or toluidine are commonly used It is also possible to employ fluorogenic substrates, which yield a fluorescent product rather than the chromogenic substrates noted above. In all cases, the enzyme-labelled antibody is added to the first antibody hapten complex, allowed to bind, and then the excess reagent is washed away. A solution containing the appropriate substrate is then added to the tertiary complex of antibody-antigen-antibody. The substrate will react with the enzyme linked to the second antibody, giving a qualitative visual signal, which may be further quantitated, usually spectrophotometrically, to give an indication of the amount of hapten which was present in the sample. "Reporter molecule" also extends to use of cell agglutination or inhibition of agglutination such as red blood cells on latex beads, and the like.

Alternately, fluorescent compounds, such as fluorescein and rhodamine, may be chemically coupled to antibodies without altering their binding capacity. When activated by illumination with light of a particular wavelength, the fluorochrome-labelled antibody adsorbs the light energy, inducing a state to excitability in the molecule, followed by emission of the light at a characteristic color visually detectable with a light microscope. As in the EIA, the fluorescent labelled antibody is allowed to bind to the first antibody-hapten complex. After washing off the unbound reagent, the remaining tertiary complex is then exposed to the light of the appropriate wavelength the fluorescence observed indicates the presence of the hapten of interest. Immunofluorescent and EIA techniques are both very well established in the art and are particularly preferred for the present method. However, other reporter molecules, such as radioisotope, chemiluminescent or bioluminescent molecules, may also be employed. It will be readily apparent to the skilled technician how to vary the procedure to suit the required purpose.

Accordingly, an aspect of the present invention contemplates a method for detecting a species of the genus Listeria in a biological sample comprising the steps of contacting said biological sample with an antibody to an enzyme or other protein or parts thereof wherein said enzyme or other protein is involved in or associated with the metabolism of a carbon source in a species of Listeria and which is absent from another species of same genus for a time and under conditions sufficient for an enzyme- or other protein-antibody complex to form and subjecting said complex to a detecting means.

The present invention contemplates that the antibody binding can be visualized by a number of methods including fluorescent staining.

In accordance with this method, the target bacteria or extracts thereof may first be immobilized onto a solid support. Where the target bacteria is immobilized, solid supports such as slides, plates, filters, beads or the like may be used. Where extracts such as protein are immobilized, solid supports such as resins can be used (resins are readility available commercially). On the other hand, protein may also be immobilized on supports such as those mentioned above for bacteria.

The present invention is also directed to a kit for the rapid and convenient assay for species of Listeria in a biological sample. The kit is compartmentalized to receive a first container adapted to contain a biological sample to be tested and a second container adapted to contain an antibody to an enzyme or protein of species of Listeria as defined above, said antibody being labelled with a reporter molecule capable of giving a detectable signal as hereinbefore described. Alternatively, if said first antibody is not labelled then a further container is provided adapted to contain a second antibody to said first antibody where said second antibody is labelled with a reporter molecule. If the reporter molecule is an enzyme, then another container adapted to contain a substrate for said enzyme is provided.

Whether by (a) genetic repair, (b) hybridization, or (c) antibody binding, the above three detection approaches require identification of enzymes, proteins or portions thereof, or identification of nucleic acid defining a promoter region, functional gene, regulatory gene or other control sequence or parts thereof for the expression of enzymes or other molecules involved in differential uptake or metabolism of the carbon sources of the present invention. Some enzymes involved in uptake or metabolism of some of these carbon sources are already known (e.g. L-lactic acid dehydrogenase, L-lactic acid oxidase, hexose phosphate phosphatase, etc.). Mutants deficient in some of these enzymes (and thus useful for transformation assays) are also known. See F. Mat-Jan et al., J. Bacterio. 171:342 (1989). Furthermore, nucleotide sequences of the genes for some enzymes (useful for the design of probes in hybridization assays) are described. E. Pradel et al., J. Bacterio. 172:802 (1990). Finally, such enzymes have been purified and antibodies have been raised against them (useful in immunological assays). M. Fatai and H. Kimura, J. Biol. Chem. 252:5820 (1977).

The present invention is further described by the following non-limiting Examples.

EXAMPLE ONE: DETECTION AND SPECIATION BY DIFFERENTIAL CARBON SOURCE METABOLISM

Using the invention described herein, species of Listeria were screened for utilization or a variety of carbon sources on the Biolog MT MicroPlate TM, a commercially available (Biolog, Inc., Hayward, Calif.) 96-well microplate designed to test the ability of an inoculated microorganisms suspension to utilize (oxidize) a panel of different carbon sources. Each well of the panel contains a tetrazolium redox dye and a buffered nutrient medium. A panel of carbon sources of the present invention was added to the MT plates and dried before inoculating with a microorganism suspension. Approximately 0.6 mg of each carbon source (e.g. 15 ul of a 4% stock solution) was added to each well. The Biolog MT MicroPlate TM was arranged so that there was one control well with no carbon source and the remaining wells contain individual carbon sources. The indicator plate was then incubated at an appropriate temperature of 37° C. for 24 hours. Many of the carbon source reactions were apparent even by 1 hours. The results are shown in Table 1.

TABLE 1

DIFFERENTIAL METABOLISM OF LISTERIA SPECIES AS MEASURED BY REDOX DYE REDUCTION ON A MICROPLATE TM TEST PANEL

| SPECIES | D-GLU-CONIC ACID L-MALIC ACID MANN-ITOL | 5' AMP | GLY-CEROL B-METH-YL GLUCO-SIDE | D-XYLOSE | L-RHAM-NOSE | XYLITOL | SU-CROSE | α-D-LAC-TOSE | L-LAC-TIC ACID | F6P G6P G1P | GEN-ERALLY PATH-OGENIC |
|---|---|---|---|---|---|---|---|---|---|---|---|
| MONO-CYTOGENES | 0 | 100 | 100 | 78$^a$ | 89$^a$ | 100 | 22 | 78$^a$ | 67 | 56 | + |
| IVANOVII | 0 | 100 | 100$^a$ | 100$^a$ | 0 | 0 | 0 | 100$^a$ | 100 | 100 | + |
| INNOCUA | 0 | 100 | 100 | 100$^a$ | 100$^a$ | 100 | 50$^a$ | 100$^a$ | 0 | 0 | − |
| WELSH-IMERI | 0 | 100 | 100 | 100$^a$ | 50$^a$ | 100 | 50$^a$ | 100$^a$ | 0 | 0 | − |
| SEELIGERI | 0 | 100 | 100 | 100$^a$ | 0 | 100 | 0 | 100$^a$ | 0 | 0 | − |
| GRAYI | 100 | 0 | 100$^a$ | 0 | 0 | 0 | 0 | 0 | 0 | 0 | − |
| MURRAYI | 100 | 0 | 100 | 0 | 0 | 0 | 0 | 0 | 0 | 0 | − |

The numbers in the table indicate the percentage of strains of the particular species tested that could utilize the carbon source. Superscript "a" indicates reactions that are negative or very weak after 2 hours but positive at 24 hours. From the data it is evident that some differences exist between the strains of a single species of Listeria.

The carbon sources L-lactic acid and hexose-phosphate (e.g. glucose-1-phosphate (G1P)) are of particular interest in this regard; these carbon sources are utilized by some but not all of the strains currently regarded as monocytogenes and by most if not all strains of ivanovii. Since the overwhelming number of Listeria disease cases involve these species, the ability to distinguish strains of monocytogenes and ivanovii offers the important potential to distinguish the pathogenic strains from the non-pathogenic strains.

In this regard, both L-lactic acid and hexose-phosphates are expected to be present in relatively high levels inside the human body and if they can be utilized by the Listeria it would allow the Listeria to grow more easily inside the body. It has been recently shown that utilization of L-lactic acid by *N. gonorrhoeae*, in competition with leukocytes, gives it an advantage in escaping the normal defense processes of the human immune system. B. E. Britigan et al., J. Clin. Invest. 81:318 (1988). D. J. Hassett and M. S. Cohen, FASEB Journal 3:2574 (1989).

While there has heretofore been no suggestion that utilization of hexose phosphates is involved in pathogenicity, Listeria does grow as an intracellular pathogen and glucose (and other hexoses) are phosphorylated when transported into the cell. Therefore, the level of hexose phosphate should exceed the level of free hexose and provide a growth advantage to any invading bacteria capable of utilizing hexose phosphate as a carbon source.

Other links have been found between utilization species. This literature has been discussed in a recent review (*Journal of General Microbiology*, 990 v. 136, p. 377). For example, *Corynebacterium renale* and *Proteus mirabilis* can grow in the kidneys and cause severe damage due, at least in part, to their synthesis of a urease enzyme which allows them to utilize urea. Another example is *Brucella abortus* which causes Brucellosis, resulting in fetal abortions in many animal species. Fetal tissues contain a high level of erythritol, and this bacterium is rather unusual in having the capability to utilize erythritol as a carbon source.

EXAMPLE TWO: STRAIN DIFFERENTIATION

Using the invention described herein, strains of species of Listeria were screened for growth on a variety of carbon sources on the Biolog MT MicroPlate TM, a commercially available (Biolog, Inc., Hayward, Calif.) 96-well microplate designed to test the ability of an inoculated microorganism suspension to utilize (oxidize) a panel of different carbon sources. As in Example 1, above, each well of the panel contains a tetrazolium redox dye and a buffered nutrient medium. A panel of carbon sources of the present invention was added to the MT plates and dried before inoculating with a microorganism suspension. About 0.6 mg of carbon source (e.g. 15 ul of a 4% stock solution) was added to each well. The Biolog's MT MicroPlate TM was arranged so that there was one control well with no carbon source and the remaining wells contain individual carbon sources. The indicator plate was then incubated at an appropriate temperature of 37° C. for 24 hours. Some carbon source reactions were apparent at 1 hour. The results are shown in Table 2.

TABLE 2

REACTIONS OF STRAINS OF LISTERIA SPECIES IN BIOLOG'S TEST PANEL

| SPECIES[b] | STRAIN # | D-GLUCONIC ACID L-MALIC ACID MANNITOL | 5' AMP | GLYCEROL B-METHYL GLUCOSIDE | L-RHAMNOSE | D-XYLOSE | XYLITOL | L-LACTIC ACID | F6P G6P G1P | SUCROSE | α-D-LACTOSE |
|---|---|---|---|---|---|---|---|---|---|---|---|
| MONO- | 1293 | − | + | + | +[a] | − | + | − | − | + | + |
| CYTO- | 2128 | − | + | + | − | +[a] | + | + | + | − | +[a] |
| GENES | 2144 | − | + | + | +[a] | +[a] | + | + | +[a] | + | − |
|  | 2198 | − | + | + | +[a] | +[a] | + | − | − | − | +[a] |
|  | 8276 | − | + | + | +[a] | +[a] | + | − | − | − | +[a] |
|  | 8277 | − | + | + | +[a] | +[a] | + | + | + | − | +[a] |
|  | 8278 | − | + | + | +[a] | +[a] | + | + | +[a] | − | +[a] |
|  | 8279 | − | + | + | +[a] | +[a] | + | + | + | − | +[a] |
|  | 8280 | − | + | + | +[a] | − | + | +[a] | − | − | − |
| IVAN- | 2103 | − | + | +[a] | − | +[a] | − | + | + | − | +[a] |
| OVII | 9076 | − | + | +[a] | − | +[a] | − | + | + | − | +[a] |
| IN- | 2102 | − | + | + | +[a] | +[a] | + | − | − | − | +[a] |
| NOCUA | 9075 | − | + | + | +[a] | +[a] | + | − | − | +[a] | +[a] |
| WELSH- | 2105 | − | + | + | +[a] | +[a] | + | − | − | − | +[a] |
| IMERI | 9079 | − | + | + | − | +[a] | + | − | − | +[a] | +[a] |
| SEELI- | 2104 | − | + | + | − | +[a] | + | − | − | − | +[a] |
| GERI | 9078 | − | + | + | − | +[a] | + | − | − | − | +[a] |
| GRAYI | 2101 | + | − | +[a] | − | − | − | − | − | − | − |
|  | 9074 | + | − | +[a] | − | − | − | − | − | − | − |
| MUR- | 2199 | + | − | + | − | − | − | − | − | − | − |
| RAYI | 9077 | + | − | + | − | − | − | − | − | − | − |

[a]Negative or very weak reaction after 2 hours.
[b]These are the species designations on the strain when received.

It is clear from Table 2 that the method of the present invention is able to differentiate between strains of particular Listeria species. The source of the strains is provided in Table 3.

TABLE 3

CHARACTERIZATION OF STRAINS OF SPECIES OF LISTERIA

| STRAIN # | SPECIES | SOURCE[1] | SOURCE # |
|---|---|---|---|
| 2101 | GRAYI | CCUG | EF-4983 |
| 9074 | GRAYI | ATCC | 19120 |
| 2102 | INNOCUA | FDA | L-0705 |
| 9075 | INNOCUA | ATCC | 33090 |
| 2103 | IVANOVII | FDA | KC-1714 |
| 9076 | IVANOVII | ATCC | 19119 |
| 1293 | MONOCYTOGENES | Carey |  |
| 2128 | MONOCYTOGENES | ATCC | 15313 |
| 2144 | MONOCYTOGENES | U of IL |  |
| 2198 | MONOCYTOGENES | CCUG | 1452 |
| 8276 | MONOCYTOGENES | Iowa St. | VM-4 |
| 8277 | MONOCYTOGENES | CCUG | EF-440 |
| 8278 | MONOCYTOGENES | CCUG | EF-441 |
| 8279 | MONOCYTOGENES | CCUG | EF-442 |
| 8280 | MONOCYTOGENES | CCUG | EF-444 |
| 2199 | MURRAYI | CCUG | EF-4984 |
| 9077 | MURRAYI | ATCC | 25401 |
| 2104 | SEELIGERI | FDA | CA-0705 |
| 9078 | SEELIGERI | ATCC | 35967 |
| 2105 | WELSHIMERI | FDA | CU-0705 |

TABLE 3-continued

CHARACTERIZATION OF STRAINS OF SPECIES OF LISTERIA

| STRAIN # | SPECIES | SOURCE[1] | SOURCE # |
|---|---|---|---|
| 9079 | WELSHIMERI | ATCC | 35897 |

[1]ATCC = American Type Culture Collection (type strains)
CCUG = Culture Collection University of Gothenburg, Sweden, Enevald Falsen
FDA = Food & Drug Administration Lab, Minneapolis MN, Sallie McLaughlin
IOWA ST. = Iowa State Universtiy, Paul Hartman
CAREY = Roberta Carey, St. Francis Hospital, Evanston, IL
U of IL = University of Illinois, Chicago Med Center, Paula Malloy

What is claimed is:

1. A method for detecting a species of the genus Listeria comprising:
    (a) exposing a sample suspected of containing microorganisms belonging to the genus Listeria to a metabolically effective amount of one or more carbon sources capable of being metabolized by a subset of species of Listeria, for a time and under conditions sufficient for said subset to metabolize said carbon source, wherein said carbon source is selected from the group consisting of L-malic acid, 5'AMP, xylitol, L-lactic acid, and hexose-phosphate; and
    (b) detecting any metabolism of said carbon source by assaying for respiration by said microorganisms, thereby determining the presence of said subset of species.

2. The method of claim 1 further comprising, prior to said exposing step, subjecting said sample to an enrichment treatment which will enhance the population of the genus Listeria in said sample.

3. The method of claim 1 wherein said one or more carbon sources comprise a panel of carbon sources comprised of L-lactic acid and xylitol.

4. The method of claim 1 wherein said one or more carbon sources comprise a panel of carbon sources comprised of hexose-phosphate and xylitol.

5. A test kit for the detection of a species of the genus Listeria or a strain of a species of the genus Listeria comprising at least one compartment containing at least one carbon source capable of being metabolized by a subset of species of the genus Listeria, wherein said carbon source is selected from the group consisting of L-malic acid, 5'AMP, xylitol, L-lactic acid, and hexose-phosphate.

6. A test kit for the detection of a species of the genus Listeria or a strain of a species of the genus Listeria comprising a plurality of compartments containing a plurality of carbon sources capable of being metabolized by a subset of species of the genus Listeria, wherein said carbon sources comprise a panel of carbon sources, each carbon source of said panel in separate compartments, comprising L-lactic acid and xylitol.

7. A test kit for the detection of a species of the genus Listeria or a strain of a species of the genus Listeria comprising a plurality of compartments containing a plurality of carbon sources capable of being metabolized by a subset of species of the genus Listeria, wherein said carbon sources comprise a panel of carbon sources, each carbon source of said panel in separate compartments, comprising hexose-phosphate and xylitol.

8. A method for detecting L. monocytogenes and L. ivanovii comprising:
    (a) exposing a sample suspected of containing microorganisms belonging to the genus Listeria to a metabolically effective amount of one or more carbon sources capable of being metabolized by L. monocytogenes and L. ivanovii but not for metabolism by other species of Listeria, for a time and under conditions sufficient for metabolism by L. monocytogenes and L. ivanovii, wherein said carbon source is selected from the group consisting of L-lactic acid and hexose-phosphate; and
    (b) detecting any metabolism of said carbon source, thereby determining the presence of L. monocytogenes and/or L. ivanovii.

9. The method of claim 8 further comprising, prior to said exposing step, subjecting said sample to an enrichment treatment which will enhance the population of the genus Listeria in said sample.

10. A method for distinguishing between the species L. monocytogenes and L. ivanovii comprising:
    (a) exposing a sample suspected of containing said microorganisms L. monocytogenes and L. ivanovii to a metabolically effective amount of the carbon source xylitol which is capable of being metabolized by L. monocytogenes but not L. ivanovii, for a time and under conditions sufficient for metabolism by said subset of species; and
    (b) detecting any metabolism of said carbon source, thereby distinguishing between the species of L. monocytogenes and L. ivanovii.

11. The method of claim 10 further comprising, prior to said exposing step, subjecting said sample to an enrichment treatment which will enhance the population of the genus Listeria in said sample.

12. In a method for detecting microorganisms of the genus Listeria wherein a sample suspected of containing microorganisms belonging to the genus Listeria is subjected to an enrichment treatment capable of enhancing the population of the genus Listeria in said sample, the improvement comprising:
    (a) thereafter exposing said sample to a metabolically effective amount of one or more carbon sources capable of being metabolized by a subset of species of Listeria, for a time and under conditions sufficient for said subset to metabolize said carbon source, wherein said carbon source is selected from the group consisting of L-malic acid, 5'AMP, xylitol, L-lactic acid, and hexose-phosphate; and
    (b) detecting any metabolism of said carbon source by assaying for respiration by said microorganisms, thereby determining the presence of said subset of species.

* * * * *

UNITED STATES PATENT AND TRADEMARK OFFICE
CERTIFICATE OF CORRECTION

PATENT NO. : 5,134,063
DATED : 7/28/92
INVENTOR(S) : Barry Bochner

It is certified that error appears in the above-identified patent and that said Letters Patent is hereby corrected as shown below:

ON THE TITLE PAGE, IN THE TITLE:

In the Title, please delete "METHODS FOR DETECTION, IDENTIFICATION AND SPECIFICATION OF LISTERIAS" and insert z--METHODS FOR DETECTION, IDENTIFICATION AND SPECIATION OF LISTERIAS--.

In col. 1, after the Title and before Field of the Invention, please insert --The invention described herein was made in the course of or under grants from the United States government.--.

In col. 1, line 5, please delete "FIELD OF THE INVETNION" and insert --FIELD OF THE INVENTION--.

In col. 1, line 28, please delete "For example, in 981" and insert --For example, in 1981--.

In col. 1, line 56, please delete "These methdos" and insert --These methods--.

In col. 2, line 10, please delete "(probes to rRNA of L. monocyvtogenes);" and insert --(probes to rRNA of L. monocytogenes);--.

In col. 2, line 17, please delete "U.S. Ser. No. 36,619" and insert --U.S. Ser. No. 839,619--.

UNITED STATES PATENT AND TRADEMARK OFFICE
CERTIFICATE OF CORRECTION

PATENT NO. : 5,134,063
DATED : 7/28/92
INVENTOR(S) : Barry Bochner

It is certified that error appears in the above-identified patent and that said Letters Patent is hereby corrected as shown below:

In col. 3, line 65, please delete "the group congsisting of" and insert --the group consisting of--.

In col. 4, line 42, please delete "but not limited to, L. monocytoqenes." and insert --but not limited to L. monocytogenes.--.

In col. 4, line 43, please delete "L. welshimeri, L. seeligeri, L. gravi" and insert --L. welshimeri, L. seeligeri, L. grayi--.

In col. 6, line 46, please delete "seeligeri, L. gravi and L. murravi" and insert --seeligeri, L. grayi and L. murrayi--.

In col. 6, line 49, please delete "L. oravi and L. murravi;" and insert --L. grayi, and L. murrayi;--.

In col. 6, line 51, please delete "differentiate L. oravi and L. murravi" and insert --differentiate L. grayi and L. murrayi--.

In col. 6, line 53, please delete "L-rhamnose" and insert --L-rhamnose--.

In col. 6, line 55, please delete "shimeri. from" and insert --shemeri from--.

In col. 6, line 57, please delete "L. ivanovii and L. gravi" and insert --L. ivanovii and L. grayi--.

In       7, line 29, please delete "measurable

UNITED STATES PATENT AND TRADEMARK OFFICE
CERTIFICATE OF CORRECTION

PATENT NO. : 5,134,063
DATED : 7/28/92
INVENTOR(S) : Barry Bochner

It is certified that error appears in the above-identified patent and that said Letters Patent is hereby corrected as shown below:

turbidmetrically." and insert --measurable turbidimetrically.--.

In col. 8, line 54, please delete "bacterium By "growth"" and insert --bacterium. By "growth"--.

In col. 8, line 64, please delete "about 10% (w/v).Most preferably," and insert --about 1.0% (w/v). Most preferably,--.

In col. 11, line 31, please delete "used may very" and insert --used may vary--.

In col. 11, line 57, please delete "capable of hydridizing" and insert --capable of hybridizing--.

In col. 12, line 32, please delete "and which are involved" and insert --and which is involved--.

In col. 13, line 40, please delete "spleen of lymph nodes" and insert --spleen or lymph nodes--.

In col. 16, line 20, please delete "1,2-phenylenediamine, 5-aminosalicyclic" and insert --1,2-phenylenediamine, 5-aminosalicylic--.

In col. 16, line 21, please delete "are commonly used It is" and insert --are commonly used. It is--.

In col. 18, line 10, please delete "utilization or a variety" and insert --utilization of a variety--.

UNITED STATES PATENT AND TRADEMARK OFFICE
CERTIFICATE OF CORRECTION

PATENT NO. : 5,134,063
DATED : 7/28/92
INVENTOR(S) : Barry Bochner

It is certified that error appears in the above-identified patent and that said Letters Patent is hereby corrected as shown below:

In col. 18, line 14, please delete "microorganisms suspension" and insert --microorganism suspension--.

In col. 18, line 27, please delete "even by 1 hours. The results" and insert --even by 1 hour. The results--.

In col. 18, line 60, please delete "*monocytogenes* and by most if not all strains of *ivanovii*." and insert --*L. monocytogenes* and by most if not all strains of *L. ivanovii*.--.

In col. 18, line 63, please delete "strains of *monocytogenes* and *ivanovii*" and insert --strains of *L. monocytogenes* and *L. ivanovii*--.

In col. 19, lines 46-47, please delete "between utilization species." and insert --between utilization of specific carbon sources and pathogenicity of a certain species.--.

UNITED STATES PATENT AND TRADEMARK OFFICE
CERTIFICATE OF CORRECTION

PATENT NO. : 5,134,063
DATED : 7/28/92
INVENTOR(S) : Barry Bochner

It is certified that error appears in the above-identified patent and that said Letters Patent is hereby corrected as shown below:

In col. 21, line 7, please delete "Gothenburg, Sweden, Enevald Falsen" and insert --Gothenburg, Sweden, Envevold Falsen--.

Signed and Sealed this

Thirteenth Day of April, 1993

Attest:

STEPHEN G. KUNIN

*Attesting Officer*  *Acting Commissioner of Patents and Trademarks*